US006187570B1

(12) United States Patent
Genders et al.

(10) Patent No.: US 6,187,570 B1
(45) Date of Patent: Feb. 13, 2001

(54) ELECTRODIALYSIS METHODS FOR PURIFICATION AND RECOVERY OF GLUCONIC ACID DERIVATIVES

(75) Inventors: J. David Genders, Marilla; Ram Gopal, Williamsville; Dan M. Hartsough, Clarence; Peter M. Kendall, East Amherst, all of NY (US); William J. Long, Charlotte, NC (US); Duane J. Mazur; Guillermo D. Zappi, both of Amherst, NY (US)

(73) Assignee: The Electrosynthesis Company, Inc., Lancaster, NY (US)

( * ) Notice: Under 35 U.S.C. 154(b), the term of this patent shall be extended for 0 days.

(21) Appl. No.: 09/318,348

(22) Filed: May 25, 1999

Related U.S. Application Data (60) Provisional application No. 60/086,792, filed on May 26, 1998.

(51) Int. Cl.[7] ............... C12P 7/40; C12P 7/58; C12P 7/60; B01D 15/04; B01D 61/42
(52) U.S. Cl. ............... 435/137; 435/136; 435/138; 435/139; 435/146; 204/518; 204/522; 204/530; 204/536; 204/537; 210/638; 210/641; 210/654
(58) Field of Search ............... 435/137, 136, 435/138, 146, 139; 204/518, 522, 530, 536, 537; 210/638, 641, 654

(56) References Cited

U.S. PATENT DOCUMENTS

| | | | |
|---|---|---|---|
| 4,057,483 | 11/1977 | Giuffrida | 204/301 |
| 4,828,993 * | 5/1989 | Sridhar | 435/136 |
| 4,882,277 * | 11/1989 | Czytko et al. | 435/136 |
| 4,885,247 | 12/1989 | Datta | 435/139 |
| 4,990,441 | 2/1991 | Barthole et al. | 435/138 |
| 5,002,881 | 3/1991 | Van Nispen et al. | 435/139 |
| 5,143,834 | 9/1992 | Glassner et al. | 435/145 |
| 5,202,476 | 4/1993 | Tsuda et al. | 562/513 |
| 5,464,760 | 11/1995 | Tsai et al. | 435/139 |
| 5,522,995 * | 6/1996 | Cockrem | 210/637 |
| 5,681,728 * | 10/1997 | Miao | 435/136 |
| 5,747,306 | 5/1998 | Oka et al. | 435/138 |
| 6,004,445 * | 12/1999 | Genders et al. | 204/537 |

FOREIGN PATENT DOCUMENTS 53-62894   6/1978   (JP).

OTHER PUBLICATIONS

Sridhar, S., Application of Electrodialysis in the Production of Malic Acid, Journal of Membrane Science, 36 (1988) 489–495.
McRae, W., Electrodialysis, Kirk–Othmer, 3rd Edition, vol. 8 (1979) 726–738.

* cited by examiner

*Primary Examiner*—Herbert J. Lilling
(74) *Attorney, Agent, or Firm*—Howard M. Ellis; Marianne Fuierer (57) ABSTRACT

A process for purifying and concentrating a gluconic acid derivative, such as 2-keto-L-gulonic acid, comprising introducing a non-viable and/or acidified fermentation medium or an in-vitro reactor medium comprising at least the gluconic acid derivative and/or salt thereof to electrodialysis thereby purifying and concentrating the gluconic acid derivative.

12 Claims, 5 Drawing Sheets

FIG. 5

ELECTRODIALYSIS METHODS FOR PURIFICATION AND RECOVERY OF GLUCONIC ACID DERIVATIVES

CROSS REFERENCE TO RELATED APPLICATION

This application claims the benefit of U.S. Provisional Application Ser. No. 60/086,792 filed May 26, 1998.

TECHNICAL FIELD

This invention relates generally to electrodialysis methods for separation and purification of preferred end products and in particular to electrodialysis methods for the purification and recovery of gluconic acid derivatives, such as 2-keto-L-gulonic acid from solutions removed from fermentation reactors and in-vitro reactors.

BACKGROUND OF THE INVENTION

A gluconic acid derivative, namely 2-keto-L-gulonic acid (hereinafter KLG), is a key intermediate in the production of valuable compounds including ascorbic acid (Vitamin C). However, to obtain high yields during the conversion of KLG to ascorbic acid, the KLG must be highly purified with a limited amount of impurities.

A convenient method for producing KLG is through a fermentation process. However, since most fermentation broths are maintained at neutral or near neutral pHs by the addition of basic substances, salts of KLG rather than KLG are produced. Furthermore, the fermentation broth also contains cells, neutrals and other undesirable materials. These additional components may interfere with the downstream chemistry used to convert KLG to ascorbic acid, therefore, the KLG must be isolated from the broth. Thus understood, any fermentation process for KLG must be integrated with an efficient recovery and purification process.

U.S. Pat. No. 5,747,306 discloses a method of separation using electrodialysis.

The viable fermentation broth is maintained at a near neutral or basic pH of between 5 and 9 by the addition of basic substances such as sodium hydroxide, potassium hydroxide or ammonia The broth is then passed through an electrodialysis tank which contains repeating cation and anion exchange membranes wherein the salts of KLG are removed from the broth. The viable fermentation broth containing neutrals, such as nutrients to insure survival of the microorganisms, is then recirculated into the fermentation system for reuse. However, the electrodialysis process produces a stream of purified KLG salt which gives lower yields during the conversion to ascorbic acid.

Additionally, the prior art process of converting organic sugars to the salt of KLG by using live and metabolically active microorganisms is complicated and demands constant vigilance to maintain a viable and active fermentation broth for the growth and/or metabolism of the microorganisms to ensure acceptable conversion of the substrate to the KLG salt.

To overcome the problems related with a high concentration of KLG salts during recovery of KLG from a fermentation medium, U.S. Pat. No. 4,990,441 discloses a method of acidifying the fermentation medium with sulfuric acid thereby precipitating the salt cation with the sulfate anion and protonating the KLG anion. However, it should be noted, that the medium containing salts of KLG also contains inorganic impurities such as phosphate and chloride anions which will also be converted to their corresponding acids with the addition of sulfuric acid. As a result, these inorganic acids can be concentrated during the KLG recovery processes, such as evaporative crystallization or direct drying and can cause acid catalyzed degradation of KLG. To rectify this problem the prior art contacts the medium containing the KLG and other impurities with a cation and anion exchange resin to remove any ionized impurities. But, neutral organics present in the fermentation broth which include simple and complex sugars may be unionized at the solution pH and thus not removed by passing the medium through cation and anion exchange resins. As such, the recovery of purified KLG is limited by the presence of these neutrals in the medium. The neutral sugars are concentrated during evaporative crystallization of KLG which causes increased viscosity of the mother liquor. As a result, multiple pass crystallization becomes difficult and KLG recovery is limited. Also, the neutrals interfere with direct drying which is a preferred method of recovery because of higher KLG yield with lower capital costs.

Accordingly, methods are needed for the concentration and purification of gluconic acid derivatives, such as KLG, which provide a higher recovery yield of KLG without the salts thereof, without contamination by inorganic impurities and neutral organics and/or without the need to maintain a fermentation medium for the growth and/or metabolism of a living and active culture of microorganisms.

SUMMARY OF THE INVENTION

For purposes of this invention, the terms and expressions below, appearing in the specification and claims, are intended to have the following meanings:

"Gluconic acid derivative" is defined as an organic acid derived from gluconic acid including, but not limited to, 2,4, keto-D-gluconic acid, 2,5, diketo-D-gluconic acid, idonic acid, 2-keto-L-gulonic acid (KLG), vanillic acid and ascorbic acid.

"Fermentation reactor" is defined as a classical fermentation reactor wherein live and viable microorganisms or cells such as bacteria are used for metabolizing carbohydrates.

"Fermentation medium " is a medium or broth derived from a classical fermentation reactor.

"In vitro reactor" is a reactor wherein enzymes being substantially free of non-living, non-viable and non-metabolizing cell structures, enzymes attached to non-living, non-viable and non-metabolizing cell structures or enzymes immobilized on a substrate have the ability to chemically oxidize and/or chemically reduce substrates or intermediates on the path to synthesizing gluconic acid derivatives.

"In vitro reactor medium" is a medium or solution derived from an in vitro reactor comprising at least a salt of a gluconic acid derivative and a coenzyme.

"Coenzyme" is an organic molecule required for the catalytic functioning of an enzyme, such as nicotinamide, adenine dinucleotide, nicotinamide adenine dinucleotide phosphate and mixtures thereof.

"Neutrals" are defined as sugars and/or compounds that are substantially unionized at the solution's pH.

"Non-viable fermentation medium" means the conditions in the fermentation broth or medium, such as pH, are such that the microorganisms used in the fermentation process are incapable of survival therein and the medium or broth may not be recirculated back into the fermentation tank for reuse without pretreatment.

"Non-living medium" means a medium removed from a fermentation reactor or in-vitro reactor such as a non-viable fermentation medium or in-vitro reactor medium wherein no living cells or living microorganisms capable of growth and/or metabolic activity for producing gluconic acid derivatives and/or salts thereof are present.

It is the principal object of this invention to provide novel electrodialysis methods for the concentration and purification of gluconic acid derivatives from an acidified and/or non-viable fermentation medium or an in-vitro reactor medium.

It is another object of the present invention to provide electrodialysis purification methods that result in higher recovery of KLG with subsequent higher yields of ascorbic acid thereby realizing lower capital and operating costs in the production of ascorbic acid.

It is a further object of the present invention to provide an electrodialysis purification method that results in a recovered product that will not be subject to acid catalyzed degradation and can make multiple passes through an evaporation crystallization recovery process because of reduced viscosity of the mother liquid.

It is still further an object of the present invention to provide an electrodialysis purification method that concentrates the end product, such as KLG, to such a high level of purity that direct drying of KLG can be employed giving near quantitative recovery of same.

It is another object of the present invention to provide an electrodialysis purification method that allows the recovery of expensive coenzymes and/or enzymes used in an in vitro reactor system for chemically synthesizing the salts of a gluconic acid derivative such as KLG.

All of the above objects may be accomplished by an electrodialysis purification method comprising the following steps of:

a) providing a non-living medium, such as an acidified and/or non-viable fermentation medium or an in vitro reactor medium comprising at least a gluconic acid derivative and/or salt thereof; and b) removing the gluconic acid derivative from the non-living medium by electrodialysis thereby providing a concentrated solution comprising at least the gluconic acid derivative.

It is an additional object of the present invention to provide processes for preparing purified and concentrated gluconic acid derivatives comprising the following steps of:

a) providing an acidified and/or non-viable fermentation medium comprising at least a gluconic acid derivative, an inorganic impurity and a neutral, wherein the gluconic acid derivative is substantially protonated;

b) removing the gluconic acid derivative and inorganic impurity from the acidified and/or non-viable fermentation medium by electrodialysis thereby providing a concentrated acidified aqueous solution comprising at least the gluconic acid derivative and inorganic impurity;

c) separating the inorganic impurity from the concentrated acidified aqueous solution thereby providing a purified and concentrated aqueous solution of the gluconic acid derivative; and d) recovering the gluconic acid derivative from the purified and concentrated aqueous solution.

The step of separating the inorganic impurity from the concentrated acidified aqueous solution may be accomplished by several methods including, but not limited to, electrodialysis and anion exchange resins. This method is particularly favorable when the acidified and/or non-viable fermentation medium contains a substantial amount of gluconic acid derivative such as KLG in the free acid form.

It is still another object of the present invention to provide processes for preparing highly purified and concentrated KLG comprising the following steps of a) providing an acidified and/or non-viable fermentation medium comprising at least KLG, an inorganic impurity and a neutral;

b) removing at least the KLG and inorganic impurity from the acidified and/or non-viable fermentation medium by electrodialysis thereby providing a concentrated acidified aqueous solution comprising at least the KLG and inorganic impurity, and a waste stream comprising a spent acidified and/or non-viable fermentation medium substantially depleted of KLG; and c) separating the inorganic impurity from the concentrated acidified aqueous solution by electrodialysis thereby providing a purified and concentrated aqueous solution of KLG.

Recovery of the purified KLG may be accomplished by any recovery method well known in the art including evaporative crystallization or direct drying.

Step (b) of the electrodialysis process may be accomplished by a first electrodialysis stack comprising:

(i) an anode in an anolyte compartment, the anode in contact with an anolyte stream, a cathode in a cathode compartment, the cathode in contact with a catholyte stream, and an electrodialysis (hereinafter ED) membrane stack disposed between the anode and the cathode. The ED membrane stack comprises at least one feed compartment, at least one concentrate compartment and alternating anion and cation exchange membranes dispersed between the feed and the concentrate compartments. The anion exchange membranes must preferentially transport KLG anions and inorganic anions to the exclusion of neutrals in the acidified fermentation medium. The acidified and/or non-viable fermentation medium is introduced into the feed compartment and an aqueous solution containing an acid or salt is introduced into the concentrate compartment. A sufficient voltage is applied across the anode and cathode such that protons or other cations migrate across the cation exchange membrane into the concentrate compartment and KLG anions and inorganic anions are transported across the anion exchange membrane into the concentrate compartment wherein a concentrated acidified aqueous solution is collected comprising at least KLG and inorganic impurities. The acidified and/or non-viable fermentation medium is essentially depleted of KLG and removed from the system as a waste stream.

Step (c) of the electrodialysis process may be accomplished by a second electrodialysis stack comprising:

i) an anode in an anolyte compartment, the anode in contact with an anolyte stream, a cathode in a cathode compartment, the cathode in contact with a catholyte stream, and an ED membrane stack disposed between the anode and the cathode. The ED membrane stack comprises at least one feed compartment, at least one concentrate compartment and alternating anion and cation exchange membranes dispersed between the feed and the concentrate compartments. The anion exchange membranes must preferentially transport inorganic anions and to the exclusion of KLG anions in the concentrated acidified solution. The concentrated acidified aqueous solution is introduced into the feed compartment and a aqueous solution containing an acid or salt is introduced into the concentrate compartment. A sufficient voltage is applied across the anode and cathode such that protons or other cations migrate across the cation exchange membrane into the concentrate compartment and inorganic anions are transported across the anion exchange membrane into the concentrate compartment. The KLG remains in the feed stream thereby providing a purified and concentrated aqueous solution of KLG.

The acidified and/or non-viable fermentation medium of the present invention preferably has a pH of less than 4.5, and more preferably less than 3.5, and most preferably less than 2 wherein the gluconic acid derivative and specifically KLG is substantially protonated. Substantially protonated as used herein means the gluconic acid derivative is at least 80% protonated and preferably greater than 90% protonated.

In an alternative embodiment, step (c) for separating the inorganic impurities may be performed before step (b) in the above process.

In the first electrodialysis stack, KLG and inorganic impurities are removed from the acidified and/or non-viable fermentation medium wherein KLG anions, as well as inorganic anions if present, are transported across an anion exchange membrane. In this instance, the membrane rejects the passage of neutrals. Hereinafter, this first electrodialysis cell is referred to as "KLG ED".

In the second electrodialysis stack, inorganic impurities such as acids or salts are separated from KLG by using anion exchange membranes which are permselective for inorganic anions but which do not transport KLG anions. The anion exchange membranes must have a very high resistance to KLG anion transport so that inorganic anions will be transported with minimal loss of KLG. Hereinafter, this second electrodialysis stack is referred to as "Desalting ED." Desalting ED refers to the removal of inorganic acids as well as inorganic salts.

It has been discovered by the inventors that an in-vitro reactor provides a more efficient and cost effective method for producing KLG if the coenzymes used as redox cofactors in the chemical synthesis of gluconic acid derivatives can be reused by returning the coenzymes to the in vitro reactor. The advantages of using the in-vitro reactor which has no living and metabolically active cells or microorganisms in the in-vitro reactor medium are numerous including the fact that alternative metabolic pathways used by living cells are shut down. Thus understood, conversion of the substrates, such as carbohydrates and/or intermediate molecules to a preferred end product is predetermined. Therefore, the substrates and/or intermediate molecules are not wasted by being converted to unwanted byproducts. Instead, the most effecient pathway of conversion is used thereby producing higher yields from the substrates or intermediate molecules to the preferred gluconic acid derivative.

Using an in-vitro reactor, the cells, if any, containing oxidizing and reducing enzymes are dead and/or non-existent and conversion to a gluconic acid derivative salt is strictly by a chemical redox reaction. However, coenzymes, used as redox cofactors in the chemical synthesis of gluconic acid derivatives, are needed in the reactor medium and recovery of these coenzymes is essential because of the high cost of replacement. With this in mind, the inventors have discovered a method using electrodialysis to recover these expensive and valuable coenzymes for reuse or recirculation back into the reactor vessel.

Thus understood, it is yet another object of the present invention to disclose processes for preparing highly purified and concentrated KLG comprising the following steps of:

a) providing an in vitro reactor medium comprising at least a gluconic acid derivative anion, a metal counterion and a coenzyme; and b) introducing the in vitro reactor medium to an electrodialysis cell comprising at least one bipolar membrane wherein the gluconic acid derivative anion is protonated and the metal counterion adds a hydroxide ion thereby providing at least a concentrated aqueous solution comprising a gluconic acid derivative and a stream comprising a metal hydroxide solution. In addition a separate stream comprising the coenzyme may be included in the process.

Several different bipolar membrane electrodialysis (ED) stacks may be used in this embodiment including a two or three compartment bipolar membrane electrodialysis stack The two compartment stack comprises an anode in an anolyte compartment, the anode in contact with an anolyte stream, a cathode in a cathode compartment, the cathode in contact with a catholyte stream, and a two compartment bipolar membrane ED stack disposed between the anode and the cathode. The two compartment bipolar membrane ED stack comprises at least one anion exchange membrane, a bipolar membrane positioned on opposite sides of the anion exchange membrane and spaced sufficiently to provide at least one feed compartment and at least one concentrate compartment, the anode and cathode positioned on different ends of the cell connected to a power source for providing an electric current through the cell stack. The anion exchange membranes must preferentially transport gluconic acid derivative anions, such as KLG anions, and inorganic anions to the exclusion of neutrally charged molecules. The in-vitro reactor medium containing at least the salt of a gluconic acid derivative is introduced into the feed compartment. Water or an aqueous solution of a gluconic acid derivative or a salt thereof is introduced into the concentrate compartment. A voltage is applied across the anode and cathode sufficient to dissociate water to form a proton and hydroxide ion at the bipolar membranes and to transport the gluconic acid derivative anion across the anion exchange membrane into the concentrate compartment of the bipolar membrane ED stack. Gluconic acid derivative anions are transported across the anion exchange membrane while the passage of neutrals are prevented. The gluconic acid derivative anion is converted to its acid form once it has been transported into the concentrate or acid compartment by the addition of proton formed at a bipolar membrane. The cation originally associated with the gluconic acid derivative anion in the feed solution is converted to a base by addition of the hydroxide ion formed at the bipolar membrane. The net effect is the formation of concentrated and purified gluconic acid derivative, such as KLG and a base, for example caustic soda, from the splitting of the KLG Na salt.

In the two compartment configuration, the hydroxide ion which displaces the KLG anion may be neutralized by the addition of $CO_2$ into the feed solution so that the pH in the feed compartment remains in a range where base catalyzed decomposition of remaining KLG does not occur. As a result, the products of the two-compartment configuration are a purified and concentrated solution of KLG and a solution comprising at least one or all of the following including a metal carbonate or bicarbonate, a metal hydroxide, and coenzymes.

The three compartment bipolar membrane ED stack is comprised of a feed or diluent compartment disposed between a base compartment and a concentrate compartment; the base compartment is separated from the feed compartment by a cation exchange membrane; and the concentrate compartment separated from the feed compartment by an anion exchange membrane. These three compartment units are bounded on the ends by bipolar membranes, which supply hydroxide ions to the base compartment and protons to the concentrate compartment. The three compartment bipolar membrane ED stack consists of at least one group of these three compartment units disposed between an anode and a cathode. In the three-compartment configuration, a hydroxide ion is introduced to the base compartment where it combines with a cation which migrates across the cation exchange membrane from the feed compartment. Therefore, the addition of a buffering agent such as $CO_2$ to the base is not necessarily needed because the feed solution of a gluconic acid derivative, such as KLG is isolated from the base by the cation membrane. In the alternative, $CO_2$ may be included if the preferred end product in the base solution is a carbonate or bicarbonate. Thus, the products of the three-compartment configuration are a purified and concentrated solution of KLG in the concentrate compartment, a solution of metal hydroxide from the base compartment and a stream containing at least a coenzyme that may be collected and reused or recirculated back into the reactor vessel. If there are any neutrals included in the feed solution, they remain therein.

Common to both the two and three compartment configurations is the anion exchange membrane, which must have a low resistance to gluconic acid derivative anion transport and should be selective for gluconic acid derivative anion transport over the transport of any neutrals that may be found in the feed solution.

A purified solution of a gluconic acid derivative, such as KLG is produced which is suitable for recovery by further processing via evaporative crystallization or other recovery techniques, such as direct drying including spray drying or thin film evaporation. If unwanted inorganic acids are removed, a higher recovery of KLG is expected because the potential for acid catalyzed decomposition of KLG upon concentration is removed. The separation of organic impurities such as neutrals from the KLG allows greater recovery of KLG because any increased viscosity that may be due to inclusion of neutrals is reduced during evaporation. Furthermore, KLG that has been purified by ED may be spray dried without suffering loss of yield during downstream conversion to ascorbic acid.

DESCRIPTION OF THE PREFERRED EMBODIMENTS

In one embodiment of the present invention, wherein the feed solution is an acidified and/or non-viable fermentation medium, the gluconic acid derivative and or salt thereof, such as KLG, may be produced by live microorganisms metabolizing carbohydrates in a fermentation process. Any microorganism capable of converting carbohydrates to a gluconic acid derivative or the salt thereof and specifically 2-keto-L-gulonic acid or salt thereof may be used in the present invention.

Before concentration and purification of a gluconic acid derivative such as KLG, the fermentation broth is preferably pretreated by any one or all of the following: (i) filtration or centrifuge to remove any microbial cells and other particulates; (ii) acidification by addition of an acid, such as sulfuric acid that serves to protonate the KLG and to precipitate the majority of cations that were introduced into the broth during the fermentation process (used to maintain an acceptable pH level for ensuring viability of the microorganisms) thereby providing a non-viable and/or acidified fermentation medium; (iii) carbon treatment to adsorb color bodies and other organic impurities; (iv) cation exchange resins, such as Amberlite IRC 120, Amberlite 200 C to more completely protonate any remaining KLG anions and/or to remove soluble cations, such as calcium; (v) anion exchange resins, such as Amberlite IRA 93, Amberlite IRA 94 to remove inorganic or organic impurities which may foul the ED membranes; (vi) treatment with polymeric adsorbent resins to remove impurities; and (vii) removal of inorganic acids or salts such as sulfuric acid by desalting ED (see description of FIG. 2). Also, a stable anion or cation exchange resin or mixtures thereof may be added to the feed solution compartment to provide enhanced mass transport of the inorganic ions to the membrane surfaces (if included in the feed solution).

Figure 1:
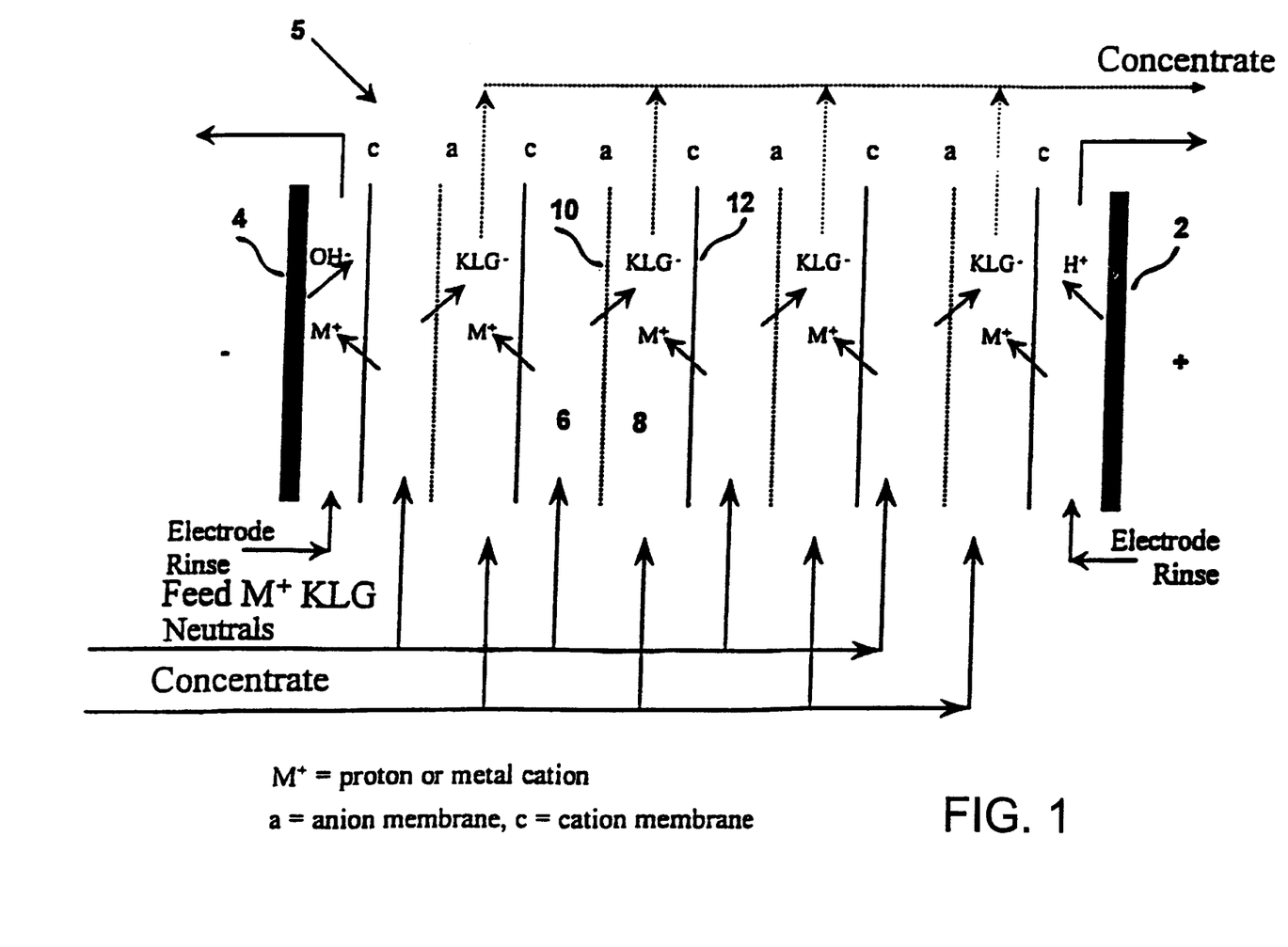
FIG. 1 is a diagrammatic view of the ED membrane cell used for separating an acidified and/or non-viable fermentation medium comprising at least a gluconic acid derivative and specifically KLG (KLG ED) from any neutrals in the medium.

If the solution has already been treated by evaporative crystallization for recovery of KLG, then the electrodialysis cell of FIG. 1 may be used on the crystallization mother liquor to remove neutrals and to allow further concentration and recovery of KLG.

The fermentation broth which is acidified and/or essentially non-viable is introduced into an electrodialysis stack such as represented in FIG. 1. The KLG ED process and the ED cell stack are used for removing at least KLG from the acidified and/or non-viable fermentation broth while leaving neutrals in the non-viable fermentation broth. The components of the KLG ED stack include an anode (2) and cathode (4) rinsed with an electrolyte, and an electrodialysis cell stack (5) comprising at least one feed compartment (6) and one concentrate compartment (8) disposed between the anode and cathode, the at least one feed and concentrate compartment are separated by alternating anion and cation exchange membranes, (10) and (12) respectively.

The anode (2) should be stable to the electrodialysis conditions and may include carbons such as graphite, noble metals or alloys of Pt, Pd, Ir, Au, Ru, etc., noble metals or alloys deposited on a valve metal such as Ti or Ta, etc. Generally, the anode reaction will be the oxidation of water to produce oxygen and protons (Equation 1).

$$2H_2O \rightarrow O_2 + 4H^+ + 4e^- \tag{1}$$

The cathode (4) may include carbons, noble metals and alloys, nickel, steels, etc. Generally, the cathode reaction is the production of hydrogen and hydroxide from the reduction of water according to reaction 2.

$$2H_2O + 2e^- \rightarrow H_2 + 2OH^- \quad (2)$$

The anode and cathode are rinsed with an electrolyte and typically the anolyte and catholyte solutions are a solution of an inert strong acid, base, or salt such as sulfuric acid, sodium hydroxide, or sodium sulfate.

Introduced into the feed compartment (6) is a feed electrolyte solution comprising an acidified and/or a non-viable fermentation medium comprising at least a gluconic acid derivative such as KLG.

Introduced into the concentrate compartment (8) shown in FIG. 1 is a concentrate solution that initially comprises deionized water, or a solution of KLG or salt thereof dissolved in water in a sufficient amount to provide conductivity in the solution.

The KLG ED cell stack diagramed in FIG. 1 is further comprised of at least one alternating anion (10) and cation (12) exchange membrane separating the feed and concentrate compartments. The cation exchange membranes may be of weak acidity (e.g. carboxylic acid type), moderate acidity (e.g. phosphonic acid type), or strongly acidic (sulfonic acid cation exchange groups). The cation membranes must be stable to the electrodialysis conditions, should have a low resistance in the gluconic acid derivative solution to be dialyzed, and may include perfluorinated membranes such as DuPont Nafion® or any non-perfluorinated cation exchange membrane such as Neosepta CMX both of which are commercially available. The anion exchange membranes may be strongly, mildly, or weakly basic and are typically comprised of quaternary or tertiary ammonium groups. The anion exchange membranes must also be stable in the conditions of the stack and should have a sufficiently open pore structure such that gluconic acid derivative anion transport can occur at reasonably low potentials. Furthermore, the anion exchange membrane should substantially prevent transport of any neutrals present in the feed stream. A preferred anion exchange membrane is Neosepta AFX. A plurality of these two compartment units comprised of anion and cation exchange membranes may be stacked together in an electrodialysis stack with at least a pair of electrodes at the outer and opposite ends of the cell.

Under the influence of a potential field, the voltage determinant upon the number of pairs of membranes and preferably ranging from 0.1 to 10 volts per pair, the cations will migrate towards the cathode (4) through the cation exchange membrane (12) into the concentrate compartment (8). The anion of the gluconic acid derivative, and specifically KLG anions, will migrate towards the anode (2) across the anion exchange membrane (10) into the concentrate compartment (8) forming a purified and concentrated solution of KLG in the concentrate and leaving behind the neutrals in the feed solution. In this manner, KLG may be nearly completely removed from the feed solution, concentrated by a actor of up to approximately 3–4 times or more, and separated from any neutrals. As a result of the separation of KLG from neutrals in the feed stream, recovery of KLG by direct drying of the concentrate may be practiced.

Figure 2:
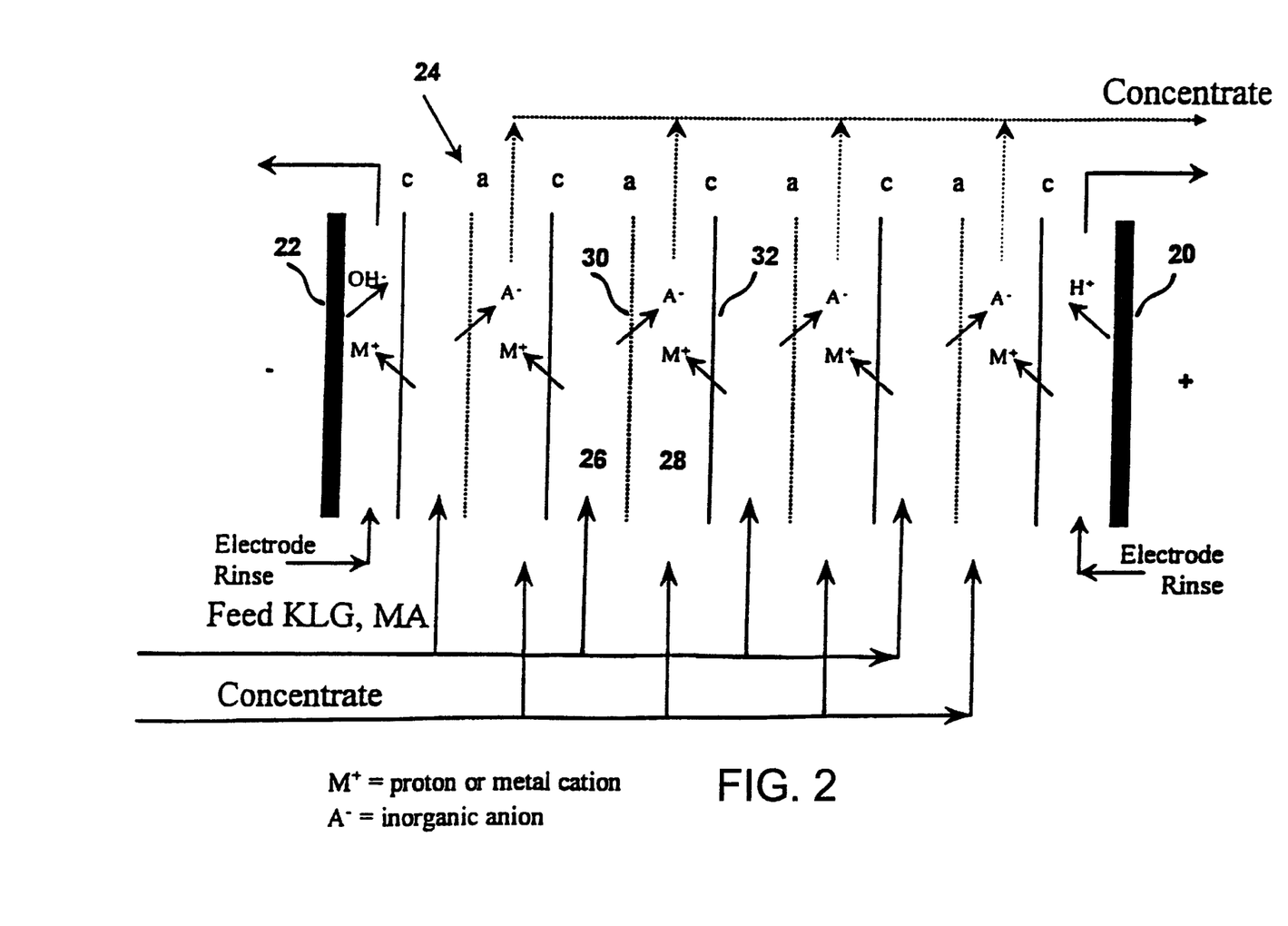
FIG. 2 is a diagrammatic view of the ED membrane cell used for separating inorganic impurities from an acidified and/or non-viable fermentation medium comprising at least a gluconic acid derivative, such as KLG (Desalting ED).

Any inorganic anions present such as chloride, sulfate, or phosphate will be transported preferentially over the transport of a gluconic acid derivative anion into the concentrate. If the inorganic anions are present as acids in the concentrate, the buildup of inorganic acids in the KLG ED concentrate may initiate proton back-migration. This back-migration may be prevented by any of the following means: (i) addition of a strong base such as sodium hydroxide to the concentrate in an amount sufficient to neutralize the inorganic acids; (ii) inorganic acids are removed in a first cut of the concentrate which is largely free of the gluconic acid derivative because the inorganic acids are transported preferentially to the gluconic acid derivative; (iii) anion exchange resins for removal of strong acids from the concentrate; and (iv) concurrent operation of a Desalting ED stack to remove inorganic acids from the concentrate nearly as quickly as they build up by feeding the concentrate from the KLG ED stack to a Desalting ED stack (as shown in FIG. 2). These four techniques all prevent the buildup of strong acids in the concentrate and subsequent proton back-migration across the anion exchange membrane which may cause a loss in current efficiency. As a further benefit, the acid catalyzed decomposition of a gluconic acid derivative, such as KLG is avoided during evaporative crystallization or direct drying.

The KLG ED cell stack diagramed in FIG. 1 may be operated at a unit cell voltage from about 0.1 to about 10 volts per anion/cation exchange membrane pair and more preferably from about 0.5 to about 3 volts per pair. The temperature range should be between about 5° C. to about 90° C. and more preferably from about 20° C. to about 50° C. Higher temperatures may cause degradation of some of the membranes and of the gluconic acid derivative, and therefore should be avoided. The process may be run continuously or in a batch mode.

One of the preferred processes for separating inorganic impurities from the concentrate solution of a gluconic acid derivative, and specifically KLG, is shown in FIG. 2. This figure diagrams the Desalting ED process and the membrane configuration in the ED membrane cell stack used for separating inorganic acids or salts from an acidified and/or non-viable fermentation medium comprising KLG or the concentrate of KLG produced in the electrodialysis cell shown in FIG. 1. The components of the electrodialysis stack include an anode (20) and cathode (22) rinsed with an electrolyte, and an electrodialysis cell stack (24) having at least one feed compartment (26) and one concentrate compartment (28) disposed between the anode and cathode wherein the feed and concentrate compartments are separated by alternating anion and cation exchange membranes, (30) and (32), respectively.

Initially introduced into the concentrate compartment (28) of the desalting ED stack is either deionized water or a solution of inorganic acid or salt dissolved in water. Introduced into the feed compartment (26) is a feed electrolyte solution which may include; a non-viable and/or acidified fermentation medium; a solution of the preferred gluconic acid derivative and/or the salt of the derivative dissolved in water; or the concentrate solution obtained from the electrodialysis cell shown in FIG. 1 comprising at least a gluconic acid derivative, such as KLG, and inorganic impurities.

Typically, the feed solution will be derived from a fermentation broth which has been rendered acidified and/or non-viable and may comprise any one or all of the following including debris from non-living microorganisms such as cells, neutrals, alkali cations, and inorganic acids. Pretreatment steps for the feed solution may comprise any one or all of the following: (i) filtration to remove cells and other particulates; (ii) acidification by addition of a convenient acid such as sulfuric acid that serves to protonate the salt of a gluconic acid derivative, such as KLG and to precipitate the majority of cations such as calcium sulfate (if the KLG was present as the calcium salt prior to acidification) and providing a non-viable and/or acidified fermentation medium; (iii) carbon treatment to adsorb color bodies and other organic impurities; (iv) cation exchange to more completely protonate the salt of a gluconic acid derivative and/or to remove soluble calcium; (v) anion exchange to remove impurities which may foul the ED membranes; (vi) treatment with polymeric adsorbent resins to remove impurities; (vii) evaporative crystallization; and (viii) removal of neutrals by the electrodialysis stack described in FIG. 1. Also, a stable anion or cation exchange resin or mixtures thereof may be added to the feed electrolyte solution compartment to provide enhanced mass transport of the inorganic ions to the membrane surfaces.

The desalting ED cell stack is further comprised of at least one alternating anion (30) and cation (32) exchange membrane separating the feed and concentrate compartments. The cation exchange membranes may be of weak acidity (carboxylic acid exchange groups), moderate acidity (e.g. phosphonic acid type), or strongly acidic (e.g. sulfonic acid cation exchange groups). The cation exchange membranes must be stable to the conditions used in electrodialysis cell, should have a low resistance in the solution to be dialyzed, and may include perfluorinated membranes such as DuPont Nafion® or any non-perfluorinated cation exchange membrane such as Neosepta CMX. The anion exchange membranes may be strongly, mildly, or weakly basic and comprised of quaternary or tertiary ammonium groups. The anion exchange membranes must also be stable and should have a sufficiently tight pore structure such that inorganic anions such as chloride or sulfate will transport through the membrane while transport of a gluconic acid derivative anion is substantially or entirely prevented. Furthermore, if removal of inorganic acids is desired, the anion exchange membrane should preferably be a low proton back-migration type such as Asahi Glass Selemion AAV or Neosepta ACM. This type of membrane will improve the current efficiency of the process by preventing back-migration of protons from the concentrate compartment to the feed compartment.

Alternatively, the inorganic acids in the concentrate compartment may be neutralized with a strong base such as sodium hydroxide so that proton back-migration is prevented.

Many of these two compartment units comprised of anion and cation membranes may be stacked together in an electrodialysis stack with at least a pair of electrodes at the outer ends.

Under the influence of a potential field, cations will migrate towards the cathode (22) through the cation exchange membrane (32) into the concentrate compartment (28). Inorganic anions will migrate towards the anode (20) across the anion exchange membrane (30) into the concentrate compartment (28) forming a solution of inorganic acid or salt and leaving behind a purified solution of a gluconic acid derivative in the feed solution (if the original feed solution is the concentrate from the electrodialysis stack described in FIG. 1). When the inorganic anions are depleted, the cell current will drop to nearly zero because the gluconic acid derivative anions that remain in the feed are substantially prevented from transporting through the anion exchange membrane by the structure of the membrane.

The Desalting ED cell stack diagramed in FIG. 2 may be operated at a unit cell voltage from about 0.1 to about 10 volts per anion/cation exchange membrane pair and more preferably from about 0.5 to about 3 volts per pair. The temperature range should be between about 5° C. to about 90° C. and more preferably from about 20° C. to about 50° C. Higher operating temperatures may cause degradation of the membranes and of the gluconic acid derivative. The process may be run continuously or in a batch mode.

Figure 3:
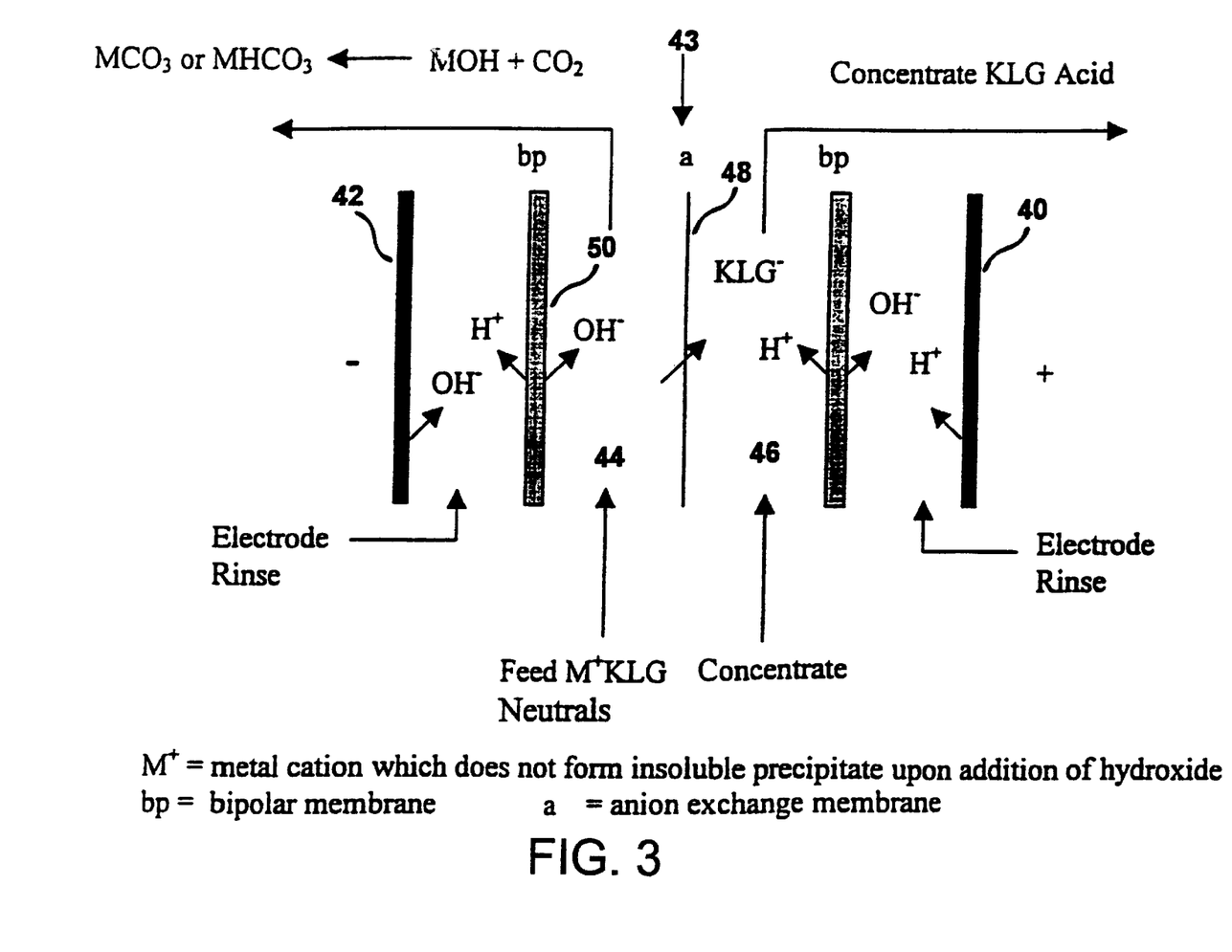
FIG. 3 is a diagrammatic view of the two compartment bipolar membrane ED cell used for the concentration and purification of a gluconic acid derivative, such as KLG from a viable or non-viable fermentation medium; or an in-vitro reactor medium(Salt Splitting KLG ED).
Figure 4:
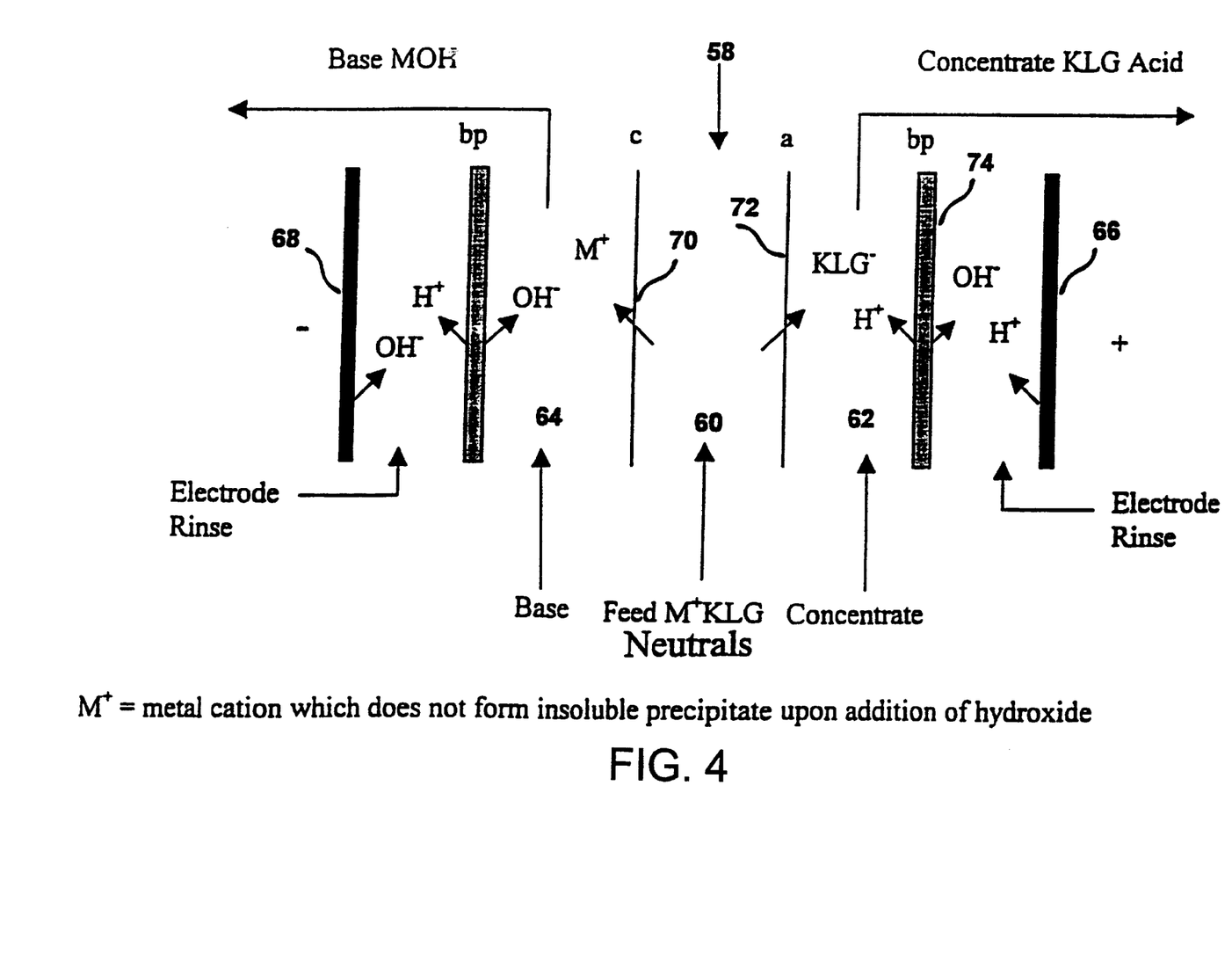
FIG. 4 is a diagrammatic view of the three compartment bipolar membrane ED cell used for the concentration and purification of a gluconic acid derivative and specifically KLG from a viable or non-viable fermentation medium (Salt- Splitting KLG ED).
Figure 5:
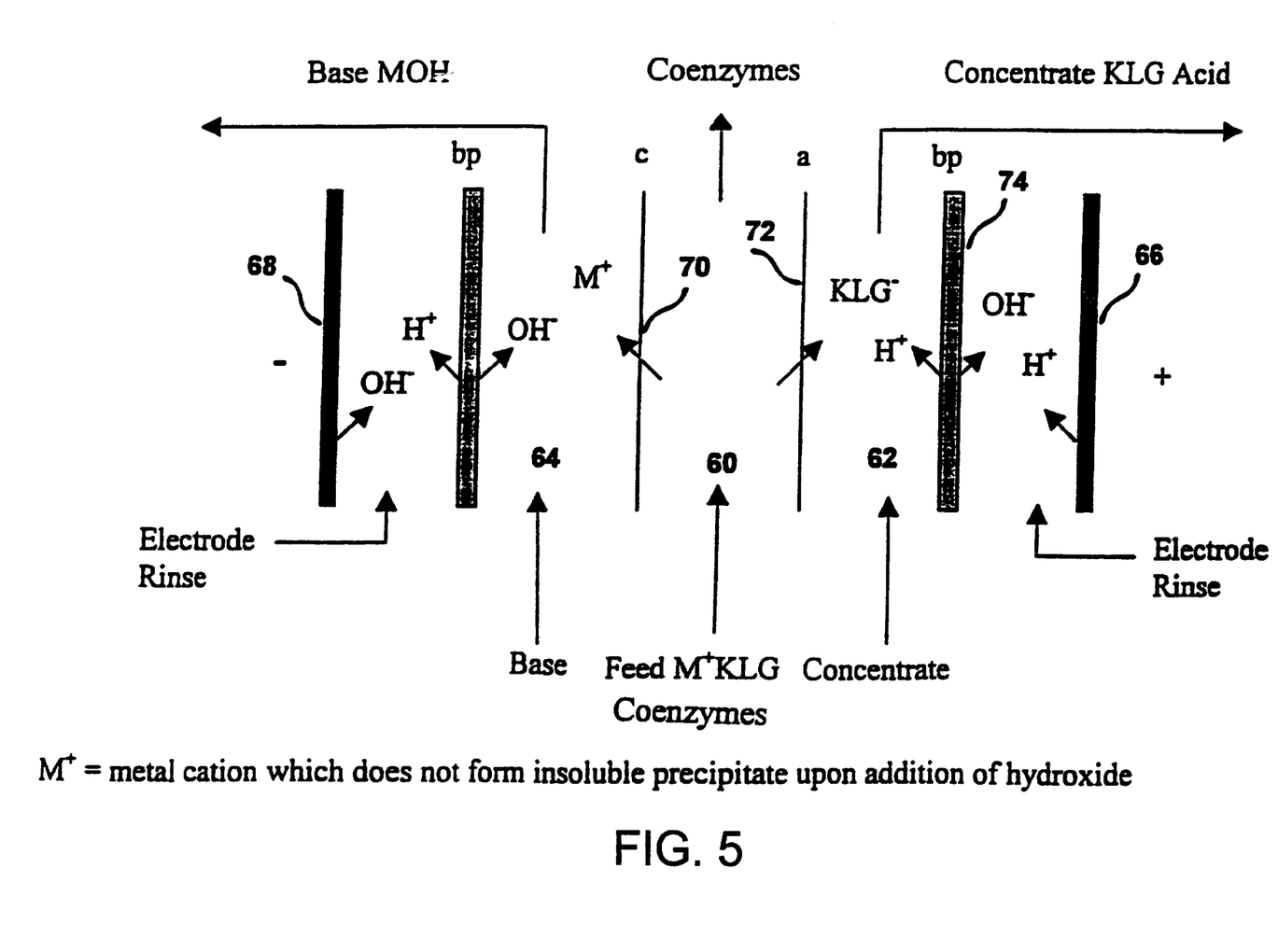
FIG. 5 is a diagrammatic view of the three compartment bipolar membrane ED cell used for the concentration and purification of a gluconic acid derivative and specifically KLG from an in-vitro reactor medium (Salt- Splitting KLG ED).

FIGS. 3, 4 and 5 diagram the Salt-splitting KLG ED processes and the two or three compartment bipolar membrane ED cell stacks used therein. In the Salt-splitting KLG ED process, a salt of a gluconic acid derivative, such as KLG is converted to purified and concentrated KLG.

The components of the two compartment electrodialysis stack shown in FIG. 3 include an anode (40) and cathode (42) rinsed with an electrolyte, and an electrodialysis cell stack (43) having at least one feed compartment (44) and one concentrate compartment (46) disposed between the anode and cathode. The feed and concentrate compartments are separated by an anion exchange membrane (48). A bipolar membrane (50) is positioned on both sides of the anion exchange membrane.

Introduced into the feed compartment (44) of the two compartment bipolar membrane ED cell stack is a feed electrolyte solution which may include an in-vitro reactor medium comprising at least the salt of a gluconic acid derivative and coenzymes; a non-viable fermentation medium comprising at least a salt of a gluconic acid derivative; a solution containing a salt of the derivative; or a KLG salt dissolved in water. The salt of the derivative should be chosen so that it does not form insoluble precipitates upon the addition of base, otherwise, these precipitates could foul the bipolar membrane or cation membranes. Representative examples of suitable salts include alkali metal salts such as sodium and potassium, or ammonium salts.

If the feed is derived from a viable or non-viable fermentation medium, pretreatment steps for the solution shall include any one or all of the pretreatment steps discussed above including:(i) filtration to remove cells and other particulates; (ii) carbon treatment to adsorb color bodies and other organic impurities; (iii) addition of an inorganic acid such as sulfuric acid to protonate the salt of the gluconic acid derivative and precipitate the metal counterion as a sulfate rendering the fermentation medium acidified and/or non-viable (iv) addition of an alkali metal salt such as sodium sulfate or sodium carbonate that will precipitate calcium as the sulfate or carbonate and form an alkali metal salt of the gluconic acid derivative which is suitable for salt splitting ED in a bipolar membrane ED stack, (v) cation exchange to remove divalent metals that would otherwise form membrane-fouling precipitates upon contact with base; (vi) anion exchange to remove impurities which may foul the ED membranes; (vii) treatment with polymeric adsorbent resins to remove impurities; and (viii) removal of inorganic salts such as sodium sulfate by desalting ED (see description of FIG. 1).

Also, a stable anion or cation exchange resin or mixtures thereof may be added to the feed solution compartment to provide enhanced mass transport of the inorganic ions to the membrane surfaces.

Introduced into the concentrate compartment (46) of the two compartment bipolar membrane ED cell stack is a concentrate solution that can be comprised initially of deionized water or of a solution of a gluconic acid derivative which is being concentrated, such as KLG dissolved in water.

The two compartment bipolar membrane electrodialysis cell stack of FIG. 3 is further comprised of an anion exchange membrane (48) and at least one bipolar membrane (50), wherein the anion exchange membrane separates the feed and concentrate compartments. The bipolar membrane consists of an anion exchange layer bonded to a cation exchange layer, such as Neosepta BP-1 or others. This membrane dissociates water to form a hydroxide ion and a proton at a low potential. The anion exchange membrane may be strongly, mildly, or weakly basic and comprised of quaternary or tertiary ammonium groups. The anion exchange membranes must be stable to the conditions within the electrodialysis cell and should have a sufficiently open pore structure such that gluconic acid derivative anion transport can occur at reasonably low potentials. Furthermore, the anion exchange membrane should prevent transport of any neutrals. Many of these two compartment units comprised of anion and bipolar membranes may be stacked together in an electrodialysis stack with at least one pair of electrodes at the outer ends.

Under the influence of a potential field, water will be dissociated in the bipolar membrane to form hydroxide ions and protons. Hydroxide ions will migrate towards the anode (40) into the feed compartment (44) of the two compartment bipolar membrane ED cell where they will combine with a metal cation, such as $Na^+$, to form a base such as sodium hydroxide. Carbon dioxide, which may be available because it is a byproduct of the fermentation process, may also be added to the feed to neutralize the hydroxide so that the feed pH does not become so alkaline that the gluconic acid derivative is decomposed. Protons will move towards the cathode (42) into the concentrate compartment (46) where they will combine with gluconic acid derivative anions which migrate towards the anode (40) across the anion membrane (48), thereby forming a purified and concentrated solution of a gluconic acid derivative and leaving behind, in the feed solution, any neutrals and/or coenzymes. The composition of the remaining feed solution is dependent upon the initial type of medium such as an in-vitro reactor medium or an acidified and/or non-viable fermentation medium. A gluconic acid derivative, such as KLG may be nearly completely removed from the feed solution, concentrated by up to a factor of approximately 3–4 times or more. As a result of the purification of KLG subsequent recovery of KLG may be accomplished by direct spray drying of the concentrate.

The three compartment bipolar membrane ED stack (58) shown in FIGS. 4 and 5 consist of at least three compartment units disposed between an anode (66) and a cathode (68). The three compartment bipolar membrane ED stack comprises a feed or diluent compartment (60) disposed between a base compartment (64) and a concentrate compartment (62); the base compartment is separated from the feed compartment by a cation exchange membrane (70), and the concentrate compartment (62) is separated from the feed compartment (60) by an anion exchange membrane (72). These three compartment units are bounded on the ends by bipolar membranes (74), which are bathed in an anolyte and catholyte rinse stream and thereby supplying hydroxide ions to the base compartment (64) and protons to the concentrate compartment (62). The bipolar and anion membranes are further described in the description of the two compartment bipolar membrane ED cell stack above. The cation exchange membranes may be of weak acidity (e.g. carboxylic acid type), moderate acidity (e.g. phosphonic acid type), or strongly acidic (sulfonic acid cation exchange groups). The cation exchange membranes must be stable in the conditions of the bipolar membrane ED stack, should have a low resistance in the gluconic acid derivative solution to be dialyzed, and may include perfluorinated membranes such as DuPont Nafion® or any non-perfluorinated cation exchange membrane such as Neosepta CMX. Many of these three compartment units comprised of bipolar, cation exchange, and anion exchange membranes may be stacked together in an electrodialysis stack with at least one pair of electrodes at the outer ends.

Under the influence of a potential field, water will be dissociated in the bipolar membranes (74) to form hydroxide ions and protons. A hydroxide ion will migrate towards the anode (66) into the base compartment (64) of the three compartment bipolar membrane ED cell where it will combine with a metal cation which is transported from the feed compartment (60) across the cation exchange membrane (70) to form a base such as sodium hydroxide. Protons will move towards the cathode (68) into the concentrate compartment (62) where they will combine with gluconic acid derivative anions which migrate towards the anode (66) across the anion exchange membrane (72), thereby forming a purified and concentrated solution of a gluconic acid derivative, such as KLG and leaving behind any neutrals in the feed solution such as shown in FIG. 4 if the feed solution is an acidified and/or non-viable fermentation medium.

Introduced into the feed compartment (60) of the three compartment bipolar membrane ED cell stack is a feed electrolyte solution which may include an in-vitro reactor medium comprising at least the salt of a gluconic acid derivative and coenzymes; a non-viable fermentation medium comprising at least a salt of a gluconic acid derivative; a solution containing a salt of the derivative; or a KLG salt dissolved in water. The salt of the derivative should be chosen so that it does not form insoluble precipitates upon the addition of base, otherwise, these precipitates could foul the bipolar membrane or cation membranes. Representative examples of suitable salts include alkali metal salts such as sodium and potassium, or ammonium salts.

Introduced into the concentrate compartment (62) of the three compartment bipolar membrane ED cell stack is a concentrate solution that can be comprised initially of deionized water or of a solution of a gluconic acid derivative which is being concentrated, such as KLG dissolved in water. Deionized water and/or a basic aqueous solution comprising NaOH or KOH may be introduced into the base compartment (64).

In a preferred embodiment shown in FIG. 5, the feed solution comprises an in-vitro reactor medium comprising at least a salt of a gluconic acid derivative and a coenzyme wherein the valuable coenzymes remain in the feed solution and can be drawn off for reuse or recirculated into the in-vitro reactor. KLG may be nearly completely removed from the feed solution, concentrated by up to a factor of approximately 3–4 times or more.

In both the two and three compartment bipolar membrane ED stacks, if any inorganic anions are present in the feed solution they may be transported into the concentrate compartment preferentially to gluconic acid derivative anions. The inorganic anions may combine with protons formed at the bipolar membranes which will result in the buildup of inorganic acids in the concentrate and cause proton back-migration with a concomitant loss of current efficiency. This may be prevented by any of the following means: (i) addition of a strong base such as sodium hydroxide to the concentrate in an amount sufficient to neutralize the inorganic acids; (ii) the inorganic acids are removed in a first cut of the concentrate which is largely free of any gluconic acid derivatives because the inorganic acids are transported preferentially to gluconic acid derivatives; (iii) concurrent operation of a Desalting ED stack to remove inorganic acids from the concentrate nearly as quickly as they build up by feeding the concentrate from the Salt-splitting KLG ED stack to a Desalting ED stack; and (iv) anion exchange for removal of strong acids from the concentrate. These four techniques all prevent the buildup of strong acids in the concentrate and possible proton back-migration across the anion exchange membrane. As a further benefit, the acid catalyzed decomposition of gluconic acid derivatives and specifically KLG is avoided during evaporative crystallization or spray drying.

Also, a stable anion or cation exchange resin or mixtures thereof may be added to the feed solution compartment to provide enhanced mass transport of the inorganic ions to the membrane surfaces(if contained in the feed solution).

The Salt-splitting ED cell stacks diagramed in FIGS. 3, 4 and 5 may be operated at a unit cell voltage from about 0.1 to about 10 volts per set of membranes and more preferably from about 0.5 to about 5 volts per set. The temperature range should be between about 5° C. to about 90° C. and more preferably from about 20° C. to about 50° C. Higher temperatures may cause degradation of some of the membranes and the acid of the gluconic acid derivatives. The process may be run continuously or in a batch mode.

In each of the above embodiments it is possible that impurities in the feed solution may foul the membranes resulting in loss of performance. The membranes may be cleaned in place (in the ED stack) with various solutions including: (i) NaCl solutions; (ii) sodium chloride solutions at pH 12; (ii) a nitric or other mineral acid solution; and (iv) solutions i, ii or iii with a non-ionic or ionic detergent added. Other wash solutions are possible so long as they effect the necessary membrane cleaning and do not degrade the membrane performance. The clean in place (CIP) procedure may include an elevated temperature of the wash solution so long as the membranes are stable to the temperatures. The CIP procedure may also include passage of current through the ED membrane stack or current reversal; however, bipolar membrane stacks generally cannot be subjected to current reversal as this would damage the bipolar membranes.

The invention will be more clearly perceived and better understood from the following examples.

EXAMPLE 1

Removal of Inorganic Acids from KLG Fermentation Broth

In an example of Desalting ED, sulfuric, hydrochloric, and phosphoric acids were removed from a non-viable and acidified fermentation broth containing KLG using the electrodialysis stack described in FIG. 2. The KLG was originally present as the calcium salt in the broth. The broth was microfiltered to remove the cells, and sulfuric acid was added to protonate the KLG salt and to precipitate calcium cation as the sulfate. The acidified broth was then cation exchanged to completely remove calcium. The electrodialysis cell used was an Electrosynthesis Company ED-1 BP cell fitted with a platinized titanium anode and cathode, Selemion AAV low proton back-migration anion exchange membranes (Asahi Glass), and Neosepta CMX (Tokuyama) cation exchange membranes. The area of the membranes was 100 cm$^2$ each (5 pairs), and the inter-membrane gap was 0.75 mm The rinse solution was 0.2 molar sulfuric acid. The initial acid compartment solution was 350 ml of water.

The initial feed solution was comprised of 910 ml of an acidified and non-viable fermentation broth containing 91 g$^{-1}$ KLG, 153 ppm chloride, 257 ppm phosphate, and 5176 ppm sulfate, all present as the acids. The experiment was operated at a controlled cell voltage of 1.6 volts per membrane pair (11 V total cell voltage, assuming combined electrode potentials of 3 V), and a temperature of 30° C. The final feed contained less than 10 ppm chloride, 34 ppm sulfate, and 120 ppm phosphate. The total charge passed was 2790 coulombs, and the current efficiency was 76% for salts removed. The current density range for the experiment was from about 13.5 to about 1.5 mA cm$^{-2}$, with the average current density being 6.5 mA cm$^{-2}$. Only 1.2% of the KLG present in the feed was lost by transport into the acid compartment.

EXAMPLE 2

Concentration and Purification of KLG from Fermentation Broth

In an example of the KLG ED process, KLG was concentrated and purified in an electrodialysis stack similar to that described above in FIG. 1. The anion exchange membranes chosen were Neosepta AFX which is a membrane that will transport the KLG anion. The feed solution that being a non-viable and acidified fermentation medium was pretreated as follows: A fermentation broth was microfiltered to remove cells, and sulfuric acid was added to protonate the KLG salt and to precipitate the cation calcium as the sulfate. Residual calcium was then removed by cation exchange.

A total of 10 membrane pairs were used giving a membrane area of 1000 cm$^2$. The anolyte and catholyte were a solution of 0.2 molar sulfuric acid. The initial concentrate consisted of 300 ml of concentrate from a previous KLG electrodialysis experiment. The initial feed solution consisted of 3.5 L of acidified and non-viable fermentation broth containing 142.4 g l$^{-1}$ KLG. The inorganic ion concentrations were: 241 mg l$^{-1}$ Cl$^-$, 565 mg l$^{-1}$ PO$_4^{3-}$, and 1277 mg l$^{-1}$ SO$_4^{2-}$. The feed was pretreated as described above. The experiment was operated at a controlled cell voltage of 2.7 volts per membrane pair or 30 volts total cell voltage, and a temperature of 45° C. The inorganic acids which transported into the concentrate were neutralized with 50% NaOH to prevent proton back-migration. After 213 minutes, 95.1% of the KLG was removed from the feed and transported into the concentrate, giving a final KLG concentration of 435.4 g l$^{-1}$ in the concentrate. The current density range was from about 70.0 to about 8.4 mA cm$^{-2}$, with the average being 26.8 mA cm$^{-2}$. The current efficiency was 67% for KLG transport. The KLG was concentrated approximately three times by ED.

Table 1 shows sugar analyses from a typical ED run where KLG is concentrated and purified using the AFX anion exchange membrane. 95% of the KLG was transported into the concentrate, but the table shows that most of the sugars were retained in the feed.

TABLE 1

Retention of Sugars During AFX ED of KLG Broth

| Component | Retention Time, min | Initial Feed concentration, g/L (total amt, g) | Final Feed concentration, g/L (total amt, g) | % Retained in Feed |
|---|---|---|---|---|
| Maltose | 10.7 | 6.84 (23.94) | 8.97 (23.55) | 98 |
| Glucose | 12.3 | 1.97 (6.90) | 2.29 (6.01) | 87 |
| Fructose | 13.4 | 1.61 (5.64) | 1.73 (4.54) | 80 |

General ED Conditions: 3.5 L of fermentation broth electrodialyzed at 2.7 volts/pr. membranes in a 10 pr. ED stack. Broth pretreated by sulfuric acid addition to precipitate calcium sulfate, followed by cation exchange; 95% of the KLG transported.

Table 2 shows the improved recovery of KLG and yield of ascorbic acid (AsA) afforded by ED. The table shows that ED coupled with direct drying gives a better overall yield to ascorbic acid than any other recovery method. Conventional crystallization (Process B), when pushed to higher recovery of KLG (90%) by the use of multiple crop crystallization, gives a poor yield from KLG to AsA and therefore a lower overall yield. This occurs because the presence of neutrals in the broth results in viscosity buildup during multiple crop crystallization, and as a result, poor separation of neutrals from KLG in the crystallization step. The neutrals are then carried into the AsA conversion process where they cause poor yields. Direct drying of the fermentation broth without ED (Process C) suffers the same problem; neutrals in the broth contaminate the KLG and as a result yields to AsA and overall process yields are low.

ED alleviates these problems by separating the neutrals from the KLG. ED of the inorganic anions can also be used to replace anion exchange. Direct drying of the ED concentrate gives a high yield of KLG product, which is substantially free of neutrals. As a result, yield conversions to AsA are good and the overall process yields and economics are superior to the other recovery techniques. Furthermore, ED allows the use of spray drying instead of crystallization, which results in considerable capital cost savings.

EXAMPLE 3

Salt-Splitting KLG ED in a Three Compartment Bipolar Membrane Cell Stack

A potassium salt of KLG is removed from an in-vitro reactor and introduced into a three compartment bipolar membrane cell stack described in FIG. 5. The feed solution to the electrodialysis cell is an in-vitro reactor medium comprising 815 ml. of solution containing 121.7 grams per liter potassium KLG salt and 0.5 millimolar nicotine adenine dinucleotide phosphate (NADP). The electrodialysis cell is a Electrosynthesis Company ED-1 BP cell fitted with a platinized titanium anode and cathode, Neosepta BP-1 bipolar membranes, Neosepta AMX-SB anion exchange membranes, and Neosepta CMB (Tokuyama Soda) cation exchange membranes. The area of the membranes is 100 cm² each (4 sets), and the inter-membrane gap is 0.75 mm. The rinse solution was 0.2 molar potassium sulfate. The concentrate and base compartments were each filled with 200 ml of water initially.

The experiment was operated at a controlled cell voltage of 3.25 volts per set of membranes or 16 volts total cell voltage, and a temperature from about 30° to about 40° C. Above 95% of KLG is removed from the feed and transported into the concentrate where it was converted to the acid form, giving a final KLG acid. Only 1.5% of the coenzyme NADP is transported into the concentrate with the remainder in the feed solution. The current density range is from about 30.0 to about 4.6 mA cm$^{-2}$, with the average being 23.9 mA cm². The current efficiency for KLG formation is 72%.

TABLE 2

Improvement of KLG Recovery and AsA Yield with ED

| Recovery Process | CX | AX/Anion ED | Process A, B, C | Conversion to AsA | Impurity Profile | Overall Yield |
|---|---|---|---|---|---|---|
| A | 0.98 | 0.99 | 0.95 | 0.866 | <1% Inorg. salts<br>15% organic acids<br>1% neutrals | 0.80 |
| B | 0.98 | 0.99 | 0.86 | 0.907 | 3% Inorg. salts<br>0.5% organic acids<br>0.5% neutrals | 0.76 |
|   | 0.98 | 0.99 | 0.90 | 0.830 | 1% Inorg. salts<br>1% organic acids<br>8% neutrals | 0.72 |
| C | 0.98 | 0.99 | 1.00 | 0.774 | <1% Inorg. salts<br>1% organic acids<br>16% neutrals | 0.75 |

Recovery Process A = Microfilter, acidify with sulfuric acid, cation exchange, Selemion AAV ED for inorganic anion removal, Neosepta AFX ED for concentration/purification of KLG at 95% recovery, direct drying of concentrate.
Recovery Process B = Microfilter, acidify with sulfuric acid, cation exchange, anion exchange, crystallize.
Recovery Process C = Microfilter, acidify with sulfuric acid, cation exchange, anion exchange, direct drying of broth.

We claim:

1. A process for preparing a purified and concentrated gluconic acid derivative, the process comprising:
   a) providing a non-viable fermentation medium having a pH less than 3.5 comprising at least the gluconic acid derivative or a salt thereof, the gluconic acid derivative selected from the group consisting of 2,4, keto-D-gluconic acid, 2,5, diketo-D-gluconic acid, idonic acid, 2-keto-L-gulonic acid (KLG), vanillic acid and ascorbic acid; and
   b) removing the gluconic acid derivative from the non-viable fermentation medium by electrodialysis thereby providing a concentrated solution comprising at least the gluconic acid derivative and a non-viable fermentation waste stream having neutrals therein to be removed from the system.

2. The process according to claim 1 wherein the non-viable fermentation medium has a pH less than 2.0.

3. The process according to claim 1 wherein the acidified and non-viable fermentation medium further comprises inorganic impurities which are removed from the non-viable fermentation medium along with the gluconic acid derivative.

4. The process according to claim 3 further comprising separation of the inorganic impurities from the concentrated solution containing the gluconic acid derivative by electrodialysis.

5. A process for preparing a purified and concentrated gluconic acid derivative comprising the steps of:
   a) providing a non-viable fermentation medium having a pH less than 3.5 comprising at least the gluconic acid derivative selected from the group consisting of 2,4, keto-D-gluconic acid, 2,5, diketo-D-gluconic acid, idonic acid, 2-keto-L-gulonic acid (KLG), vanillic acid and ascorbic acid, an inorganic impurity and a neutral;
   b) removing the gluconic acid derivative and inorganic impurity from the non-viable fermentation medium by electrodialysis thereby providing a concentrated acidified aqueous solution comprising at least the gluconic acid derivative and inorganic impurity, and a waste stream comprising a spent non-viable fermentation waste stream containing unionized neutrals and which is essentially depleted of the gluconic acid derivative;
   c) separating the inorganic impurity from the concentrated acidified aqueous solution thereby providing a purified and concentrated aqueous solution of the gluconic acid derivative; and
   d) recovering the gluconic acid derivative from the purified and concentrated aqueous solution.

6. The process according to claim 5 wherein the non-viable fermentation medium has an acidic pH less than 2.0.

7. The process according to claim 5 wherein the step of separating the inorganic impurity from the concentrated acidified aqueous solution is effected by electrodialysis.

8. The process according to claim 7 wherein electrodialysis is conducted in a cell having a plurality of alternating cation-exchange membranes and anion-exchange membranes spaced sufficiently from each other to provide at least one feed and concentrate compartment, an anode and cathode in different end cells of the container connected to a power source for providing an electric current through the electrodialysis cell.

9. The process according to claim 7 wherein the recovering of the gluconic acid derivative is by direct drying.

10. The process according to claim 5 wherein the inorganic impurity is an inorganic acid.

11. The process according to claim 8 wherein the anion-exchange membrane used in step (b) substantially prevents transport of the neutral in the feed stream into the concentrate compartment.

12. The process according to claim 8 wherein the anion-exchange membrane used in step (c) has a sufficiently tight pore structure such that an inorganic anion will transport through the membrane while transport of a gluconic acid derivative anion is substantially or entirely prevented.

* * * * *